United States Patent [19]

Jackson et al.

[11] Patent Number: 4,495,844
[45] Date of Patent: Jan. 29, 1985

[54] ROTARY MICROTOME DRIVE

[76] Inventors: Brian L. Jackson, Foxelwood, Oakington, Cambridge CB4 5AR; Philip Parker, 6 Conley Close, Ramsey, Cambridge PE17 1EL, both of England

[21] Appl. No.: 302,415
[22] PCT Filed: Jan. 16, 1981
[86] PCT No.: PCT/GB81/00006
 § 371 Date: Sep. 15, 1981
 § 102(e) Date: Sep. 15, 1981
[87] PCT Pub. No.: WO81/02063
 PCT Pub. Date: Jul. 23, 1981

[30] Foreign Application Priority Data

Jan. 17, 1980 [GB] United Kingdom ............... 8001672

[51] Int. Cl.³ ............................................. G01N 1/06
[52] U.S. Cl. ........................................ 83/715; 83/414; 83/714; 83/915.5
[58] Field of Search ............... 83/915.5, 707, 713, 83/714, 715, 717, 414; 33/23 R, 23 C, 23 H, 23 K, 22, 192

[56] References Cited

U.S. PATENT DOCUMENTS

| 3,771,405 | 11/1973 | Blum | 83/915.5 |
| 3,785,234 | 1/1974 | Sitte | 83/915.5 |
| 3,955,638 | 5/1976 | Wasko | 177/212 |

FOREIGN PATENT DOCUMENTS 192431 11/1967 U.S.S.R. ........................... 83/915.5

OTHER PUBLICATIONS

"Handbok I Finmekanik", Bartil Ejerhed, (English translated version).

Primary Examiner—Frank T. Yost
Assistant Examiner—Hien H. Phan
Attorney, Agent, or Firm—Brisebois & Kruger

[57] ABSTRACT

A specimen table advance mechanism comprising a parallelogram linkage for a rotary microtome in which the effects of friction sticking are largely eliminated from the articulation points of the linkage by use of strip hinges.

7 Claims, 3 Drawing Figures

ROTARY MICROTOME DRIVE

This invention relates to rotary microtomes, by which is meant microtomes in which relative incremental advance movement between a specimen table and a relatively reciprocable knife, and the reciprocating movement itself are both derived from a single rotatable drive member. The typical increment of the advance movement is some 4 microns in the case of specimens embedded in paraffin wax, and some 0.5–1.0 microns in the case of samples embedded in synthetic resin.

Conventional rotary microtomes provide the advance movement by means of a leadscrew which acts on a linear dovetail slide carrying the specimen table. This provides a robust mechanism which is well able to withstand the cutting forces involved, but in practical use, the arrangement is likely to suffer from friction and sticking and attendant vibration, which interfere with the accuracy of the advance movement. This is particularly the case in rotary microtomes designed for specimens embedded in synthetic resin, since in these it is necessary to provide for specimen retraction between successive cutting strokes, in order to prevent the last-cut section from re-adhering to the sample under the effects of static electricity during the return stroke. This retraction is conventionally of some 50 microns or so, and re-setting of the specimen advance after such a retraction is rendered unreliable, particularly where, in addition to the friction and sticking effects associated with the dovetail slide referred to above, the leadscrew itself is moved bodily to permit the retraction.

The present invention is concerned to provide a specimen table advance mechanism for a rotary microtome in which the effects of friction and sticking and vibration are largely eliminated, in which the cutting forces involved are well catered for and which can be adapted for both paraffin-embedded and synthetic resin-embedded specimens without substantial re-design of the basic arrangement.

Basically the present invention provides a rotary microtome in which the advance movement of the specimen table relative to the cutting member is provided by a parallelogram linkage. As will be readily understood from the subsequent description of a specific embodiment of the invention, the parallelogram linkage may itself also act as the support for the specimen table. To eliminate friction and sticking entirely from the points of articulation of the parallelogram linkage, they may be constituted by strip hinges.

DETAILED DESCRIPTION

Figure 1:
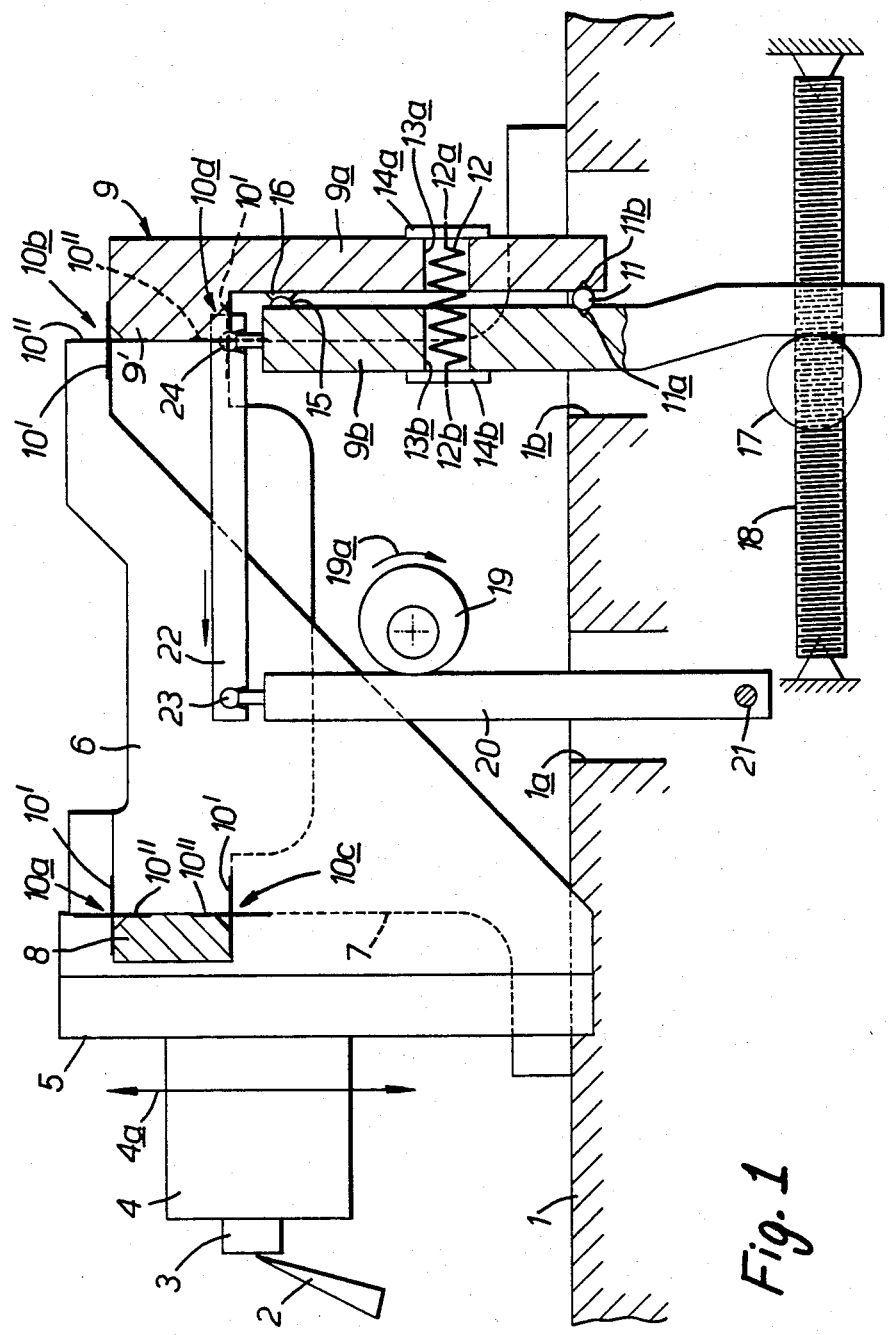
FIG. 1 is a schematic view in side elevation of the specimen table support and advance mechanism of a rotary microtome for synthetic resin-embedded specimens, with portions cut away for illustration.
Figure 2:
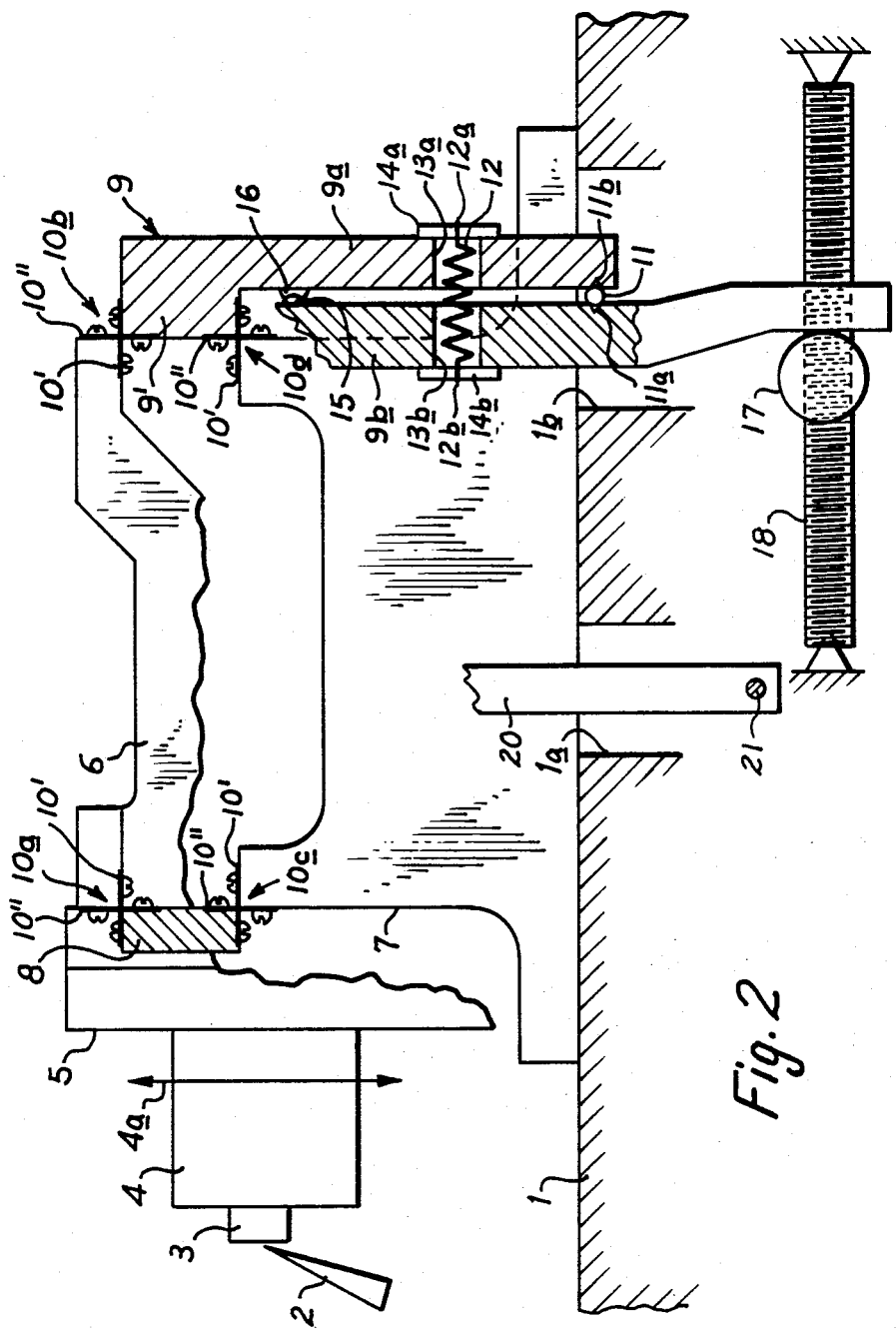
FIG. 2 is a view corresponding to FIG. 1 but with additional portions removed and cut away to more clearly illustrate the hinges.
Figure 3:
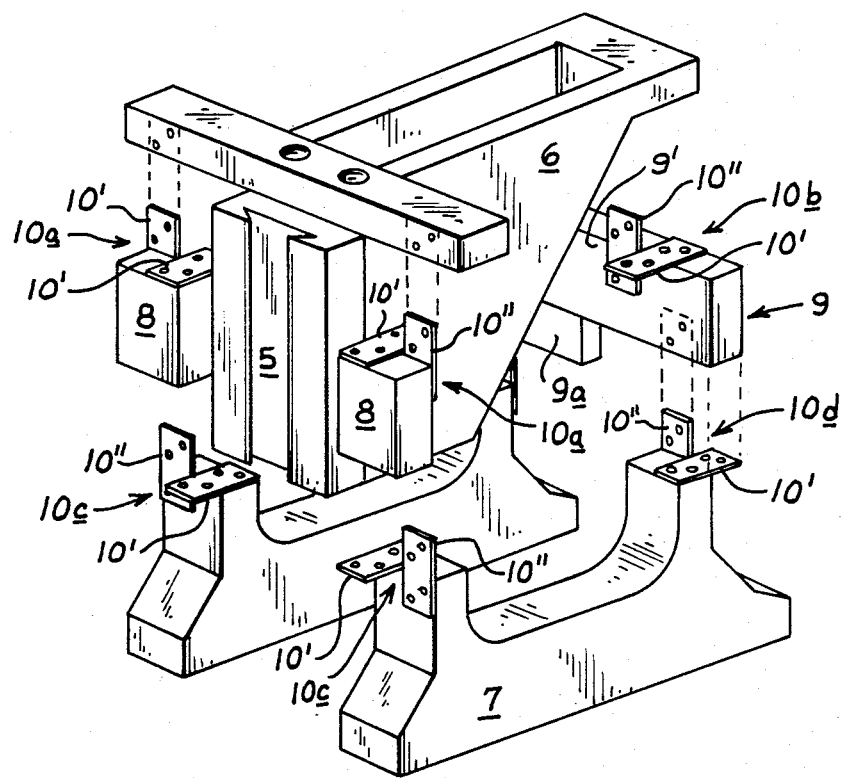
FIG. 3 is an exploded perspective view of the microtome of FIGS. 1 and 2.

The mechanism in the drawings is supported on the massive base 1 of the microtome, which base is apertured at 1a and 1b for the passage of parts of the mechanism. A knife 2 is fixed to the base by conventional means (not shown in the Figure) and a specimen 3 is shown as mounted on a specimen support 4 which is carried for reciprocating movement vertically relative to the knife (as shown by the arrow 4a) on a dovetail guide 5 which together with the specimen support 4 constitutes the specimen table of the microtome. The guide 5 is rigidly fixed to a bracket 6 which forms an upper limb or lower horizontal link of a parallelogram linkage whose lower limb is constituted by a pedestal structure 7 secured fast to the base 1. The sides of the parallelogram are formed on the one hand by a vertical link 8 adjacent the dovetail guide 5 and on the other hand by an upper vertical portion of 9' of a member generally indicated at 9 through which both advance and retraction of the specimen table are effected. Articulation of the parallelogram linkage is provided by four paired sets of crossed strip hinges indicated at 10a–d, each set having a horizontal strip 10' and a vertical strip 10" arranged orthogonally to define a unique hinge line. As is shown at FIG. 2, the upper vertical portion 9' of member 9 has a vertical height between the articulations or hinge points 10b and 10d which is the same as the height of vertical link 8 between hinge points 10a and 10c. It will be understood that for mechanical stability and balance the pair of sets of hinges at each articulation point lie one on either side of the median plane of the mechanism on which FIGS. 1 and 2 are based.

From a general inspection of the Figures, it will be appreciated that the articulation of the parallelogram linkage will permit movement of the specimen accurately parallel to the base 1 of the microtome. The movement is provided by means of the member 9 which, as can be seen in the FIGS. 1 and 2, is constructed in two parts. The first part, 9a, is articulated at 10b and 10d to the bracket 6 and pedestal structure 7 respectively, and its rotation about the articulation point 10d is used to cause the advance and retraction movements of the specimen table. The second part, 9b, of the member 9 is connected to the first part 9a in such a manner as to permit lost motion between the two. The two parts articulate about a pair of ball pivots 11 located in corresponding V-notches 11a, 11b in the respective parts, and are held normally in the relative positions shown in FIGS. 1 and 2 by means of a tension spring 12 which is accommodated within aligned bores 13a, 13b in the parts 9a and 9b, and whose ends 12a, 12b are connected to corresponding abutment members 14a, 14b by which the tension in the spring is transmitted to the parts 9a and 9b. The precise normal alignment between the parts 9a and 9b is defined by a stop 15 on the part 9b and an anvil 16 on the part 9a.

The normal orientation of the composite member 9 is defined by means of a trunnion nut 17 on a leadscrew 18 which is journalled in the base 1 and is driven in standard manner by the rotary drive of the microtome to provide the necessary advance movement of the specimen table. Such advance movement is provided by rotation of the lead screw to move trunnion nut 17 to the right, which pivots the composite parts 9a and 9b counter-clockwise as a unit about pivot 10d. It will be appreciated that the two-part member 9 could be replaced by a corresponding unitary member for a microtome in which no retraction is required. However, in the present embodiment, the microtome driving train includes a cam 19 which is rotated by the microtome drive as indicated by the arrow 19a to cause rocking movement of a lever 20 pivoted at one end to the base of the machine at 21. A link 22 is connected via ball and socket joints 23, 24 between the upper end of the lever 20 and the upper end of the second part 9b of the member 9. As cam 19 rotates, the high region of the cam 19 causes the lever 20 to pivot in an anti-clockwise direction during the return stroke of the specimen past the knife blade 2 in the direction 4a. This movement of lever 20 is transmitted to the part 9b of member 9. Consequently, part 9b rotates anti-clockwise about the trunnion nut 17, whose circular surface allows a rocking movement. As part 9b rotates anti-clockwise, part spring 12 stretches, permitting stop 15 to separate from anvil 16 while holding the lower portions of parts 9a and 9b together at the ball pivot 11. Because part 9a is connected to the hinge or articulation point 10d, which is fixed to the base via pedestal structure 7, part 9a cannot pivot anti-clockwise with part 9b. However, the pull exerted by spring 12 on part 9a is below articulation part 10d and causes part 9a to pivot clockwise to thus retract bracket 6 and specimen 3 which is mounted on this bracket. As part 9a thus pivots clockwise about articulation 10d, the parts 9a and 9b pivot relative to each other about pivot 11 which moves with the parts 9a and 9b as part 9b pivots anti-clockwise and part 9a pivots clockwise. When the cam 19 again presents its low region to the lever 20, the parts 9a and 9b return to their earlier relative alignments, with the stop 15 and anvil 16 in contact, as shown at FIG. 1, and the normal advance set by the leadscrew is accurately maintained. The dimensions of the cam 19 on the one hand, and the linkage formed by the lever 20, link 22 and part 9b of member 9 are selected to cause a retraction of some 50 microns. Normal advance of specimen 3 is caused by movement of nut 17 to the right in FIGS. 1 and 2 to pivot part 9a clockwise about fixed hinge 10d.

The use of the parallelogram linkage will be understood to enable the production of a very accurate advance motion without the problems of friction and sticking and vibration inherent in the conventional linear dovetail slide arrangement. By the use of strip hinges of a suitable material, such as the beryllium-copper alloy used in the illustrated embodiment, these causes of difficulty and error are completely eliminated, even in a rotary microtome as hereinbefore defined. More significantly, the parallelogram linkage permits the manufacture of two patterns of rotary microtome, one with retraction and one without, on the basis of a single specimen table support and advance mechanism. This allows considerable economy by reducing the overall amount of tooling necessary to produce the two patterns.

With reference to the retraction mechanism in the illustrated embodiment, this operates without movement either of the leadscrew or of its nut, so that the accuracy with which the advance movement is set is unaffected by the retraction.

In addition to the elimination of sticking and friction and the attendant vibration, the use of strip hinges in the present embodiment also achieves a considerable reduction in the amount of maintenance which is necessary during the life of the microtome.

We claim:

1. An improved rotary microtome of the type in which a specimen table and a knife are mounted for relative reciprocable movement therebetween in a first direction for cutting a slice from the specimen, and for incremental movement in a second direction to incrementally advance the specimen mounted on said specimen table and said knife relative to each other, said microtome comprising, a base, a first link connected to said base for pivotal movement about a first hinge secured to said base for pivotal movement about a first hinge secured on said base, a second link parallel to said first link and connected to said base for pivotal movement about a second hinge secured on said base and spaced from the first hinge, a third link connected to said first link at a third hinge and pivotally connected to said second link at a fourth hinge, said hinges having pivot axes parallel to each other and being located respectively at corners of a parallelogram so that pivotal movement of said first link about said first hinge in a first direction causes said third link to move parallel to a line extending through said axes of said first and second hinges, to incrementally advance the specimen and knife relative to each other, and rotatable drive means for pivoting said first link in said first direction to cause said incremental advance.

2. A microtome according to claim 1 wherein each hinge comprises a first pair of crossed strip hinges and a second pair of crossed strip hinges axially aligned with said first pair of hinges.

3. A microtome according to claim 1 further comprising means for pivoting said first link in a second direction opposite to said first direction to retract said specimen and knife relative to each other.

4. A microtome according to claim 3 wherein said retracting means comprises an arm pivoted on said first link, and spring means for pivoting said arm in said second direction in response to pivotal movement of the arm away from the first link.

5. A microtome according to claim 4 wherein said means for pivoting said arm comprises an additional link pivoted to said arm at a pivot connection aligned with said first hinge axis during said incremental advance.

6. A microtome according to claim 1 wherein said rotatable drive means comprises a leadscrew.

7. A microtome according to claim 6 further comprising a nut threaded on the leadscrew and about which said arm can rock to retract the specimen and knife relative to each other.

* * * * *